United States Patent [19]

Weyl et al.

[11] Patent Number: 5,698,084

[45] Date of Patent: Dec. 16, 1997

[54] ELECTRO-CHEMICAL MEASURING SENSOR

[75] Inventors: Helmut Weyl, Schwieberdingen; Romuald Fries, Weissach; Peter Jansing, Renningen, all of Germany

[73] Assignee: Robert Bosch GmbH, Stuttgart, Germany

[21] Appl. No.: 591,535

[22] PCT Filed: Jun. 3, 1995

[86] PCT No.: PCT/DE95/00730

§ 371 Date: Feb. 6, 1996

§ 102(e) Date: Feb. 6, 1996

[87] PCT Pub. No.: WO95/34809

PCT Pub. Date: Dec. 21, 1995

[30] Foreign Application Priority Data

Jun. 16, 1994 [DE] Germany .................. 9409684 U

[51] Int. Cl.⁶ ........................................ G01N 27/407
[52] U.S. Cl. ........................ 204/424; 204/427; 204/428
[58] Field of Search ........................... 204/421–429

[56] References Cited

U.S. PATENT DOCUMENTS

| | | | |
|---|---|---|---|
| 2,100,052 | 11/1937 | Travis | 248/314 |
| 3,835,012 | 9/1974 | Hemak | 204/428 |
| 3,960,693 | 6/1976 | Weyl et al. | |
| 4,019,974 | 4/1977 | Weyl et al. | 204/428 |
| 4,065,372 | 12/1977 | Hacker et al. | 204/428 |
| 4,145,272 | 3/1979 | Nakamura et al. | |
| 4,219,359 | 8/1980 | Miwa et al. | 204/428 |
| 4,540,070 | 9/1985 | Yonovich et al. | 267/141 |
| 4,741,816 | 5/1988 | Nishio et al. | 204/424 |
| 4,944,861 | 7/1990 | Reber | 204/427 |
| 5,246,562 | 9/1993 | Weyl et al. | 204/424 |
| 5,573,650 | 11/1996 | Fukaya et al. | 204/427 |

FOREIGN PATENT DOCUMENTS

| | | |
|---|---|---|
| 0415007 | 3/1991 | European Pat. Off. . |
| 0520528 | 12/1992 | European Pat. Off. . |
| 4312506 | 10/1994 | Germany . |
| 92/08127 | 5/1992 | WIPO . |

*Primary Examiner*—T. Tung
*Attorney, Agent, or Firm*—Spencer & Frank

[57] ABSTRACT

An electrochemical measuring sensor for determining the oxygen content of gases, such as exhaust gases of internal combustion engines, includes a housing having an annular sealing seat defined on an inner surface thereof; a sensor element which is comprised of a solid electrolyte body which is oxygen-ion conducting, which has a form of a tube having a closed end and which has an annular shoulder provided thereon; and a seal ring positioned between the annular sealing seat of the housing and the annular shoulder of the solid electrolyte body, and including a plurality of resilient elements distributed thereon. Each of the plurality of resilient elements has a lower portion and an upper portion angled toward the housing, and the seal ring has a clear width so that each lower portion rests on and is mechanically prestressed against the annular shoulder of the sensor element and each upper portion is mechanically prestressed against the housing, whereby a tight seal of the sensor element to the housing is provided and the sensor element is maintained within the housing under mechanical prestress and secure against relative rotation.

5 Claims, 2 Drawing Sheets

ELECTRO-CHEMICAL MEASURING SENSOR

BACKGROUND OF THE INVENTION

1. Field of the Invention

The invention is based on an electro-chemical measuring sensor for determining the oxygen content of gases, in particular for determining the oxygen content of exhaust gases of internal combustion engines, with a sensor element inserted into a housing with a seal ring, which has an oxygen ion-conducting solid electrolyte body in the form of a tube closed on one side. Electro-chemical measuring sensors are designed, for example, with a sensor element of a so-called finger shape, wherein a solid electrolyte body in the shape of a closed tube is sealingly fixed in place in a metallic housing. Differentiations are made in connection with finger sensors between potential-free and potential-dependent measuring sensors. With potential-dependent measuring sensors, the strip conductors of the outer electrodes are brought into contact with the housing by means of an electrically conductive sealing ring. With potential-free measuring sensors, each electrode connection is directly supplied to a control instrument, so that electrical contact with the housing is not permitted. Sealing between the solid electrolyte body and the housing must be provided in either case.

2. Description of the Related Art

Potential-free measuring sensors in particular, wherein a contact for each electrode connection is disposed on the annular surface of the solid electrolyte body, require a positionally correct seating of the contact elements. There is the danger that during the installation of the measuring sensor the solid electrolyte body is twisted after having been inserted and that therefore the contacts of the electrodes take up a different position, because of which assured contact is impossible.

A metallic sealing ring, for example, is used for sealing the solid electrolyte body in the housing, wherein with a potential-free measuring sensor the strip conductor to the outer electrode in the area of the metallic sealing ring must be covered with electrical insulation.

SUMMARY OF THE INVENTION

The measuring sensor in accordance with the invention and having the characterizing features that means are provided which maintain the sensor element in the housing under mechanical prestress, which has the advantage that the sensor element is fixed in place in the housing secure against relative rotation. By means of this a secure contact of the electrode connections is possible, particularly in connection with the mounting of potential-free measuring sensors.

Advantageous further embodiments of the measuring sensor in accordance with the invention are possible by the measures recited in the dependent claims. In particular, the means are constituted by at least one resilient element formed on the seal ring. The seal ring may have a ring element on which the resilient elements are formed evenly radially distributed. The resilient elements may be embodied with respectively one lower part and an outwardly angled off upper part and have a clear width (W) in such a way that the lower parts rest against the sensor element under mechanical prestress and the upper parts are supported under mechanical prestress on the housing. The seal ring may consist of Cr—Ni steel with an applied ductile layer of Ni or Cu. A simple fixing in place of the sensor element in the housing, which is secure against relative rotation, can be realized by means of a specially designed seal ring which maintains the sensor element in the housing under mechanical prestress. Equipping the seal ring with resilient elements has been shown to be particularly practical.

BRIEF DESCRIPTION OF THE DRAWINGS

An exemplary embodiment of the invention is represented in the drawings and explained in more detail in the following description. Shown are, in FIG. 1, a longitudinal section through the portion of the measuring sensor on the exhaust gas side.

DESCRIPTION OF THE PREFERRED EMBODIMENTS

Figure 1:
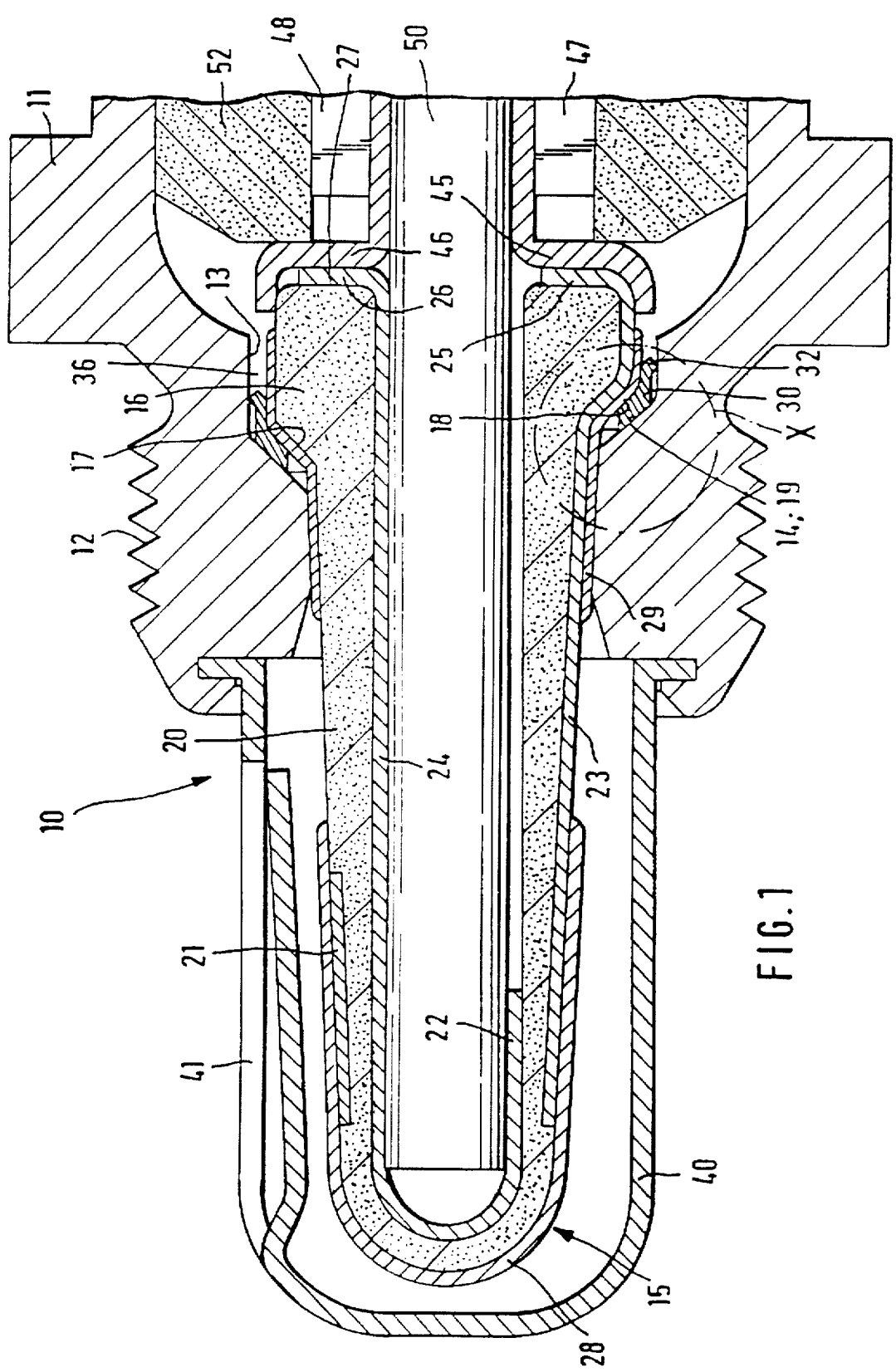

The electro-chemical measuring sensor 10 represented in FIG. 1 has a metallic housing 11, which has a thread 12 on its exterior constituting a fastening means for installation in a gas measuring tube, not shown. The housing 11 has a longitudinal bore 13 with an annular sealing seat 14 supporting a metallic seal ring 30. The sensor element 15 rests on the seal ring 30 with an annular shoulder 17 formed on a bead-shaped head 16. A sealing surface 18 on the side of the sensor element is formed on the bead-shaped head 16 between the seal ring 30 and the sensor element 15. In the area of the bead-shaped head 16, the longitudinal bore 13 is designed in such a way that a gap 36 is formed between the bead-shaped head 16 of the sensor element 15 and the housing 11. The sealing seat 14 itself forms a sealing face 19 on the housing side. The sealing zone X being formed on the seal ring 30 is shown in an enlargement in FIG. 2.

In the instant example the sensor element 15 is a tube-shaped solid electrolyte body 20, whose end section toward the gas to be measured is closed. A layered, gas-permeable measuring electrode 21 is disposed on the exterior exposed to the gas to be measured, and a layered, gas-permeable reference electrode 22, which is exposed to a reference gas, for example air, is disposed on the side facing the interior. The measuring electrode 21 is connected by means of a measuring electrode strip conductor 23 with a first electrode contact 25, and the reference electrode 22 is connected by means of a reference electrode strip conductor 24 with a second electrode contact 26. The electrode contacts 25, 26 are respectively located on a front face 27 formed by the open end of the solid electrolyte body 20. A porous protective layer 28 is placed over the measuring electrode 21 and partially over the measuring electrode strip conductor 23. The electrodes 21, 22 and the strip conductors 23, 24 are advantageously embodied as cermet layers and co-sintered with the solid electrolyte body 20.

The sensor element 15, which protrudes on the gas-measuring side from the longitudinal bore 13 of the housing 11, is surrounded at a distance by a protective tube 40, which has openings 41 for the entry and exit of the gas to be measured and is fixed in place on the end of the housing towards the gas to be measured. The interior of the sensor element is filled, for example, by a rod-shaped heating element 50 which is fixed, not shown, at the end away from the gas to be measured and is provided with line connections.

A first contact element 45 rests on the first electrode contact 25 and a second contact element 46 on the second electrode contact 26. The contact elements 45, 46 are shaped in such a way that they rest, for example, against the tube-shaped heating element 50 and are in contact with a measuring electrode connector 47 and a reference electrode connector 48. The connectors 47, 48 are connected with connection cables, not shown, and lead outward to a measuring or control instrument, also not shown.

An insulating sleeve 52 is furthermore disposed in the longitudinal bore 13 of the housing 11 and preferably is made of a ceramic material. The insulating sleeve 52 is pressed on the contact element 45, 46 by mechanical means, not shown, and the electrical connection with the electrode contacts 25, 26 is provided in this way.

Figure 2:
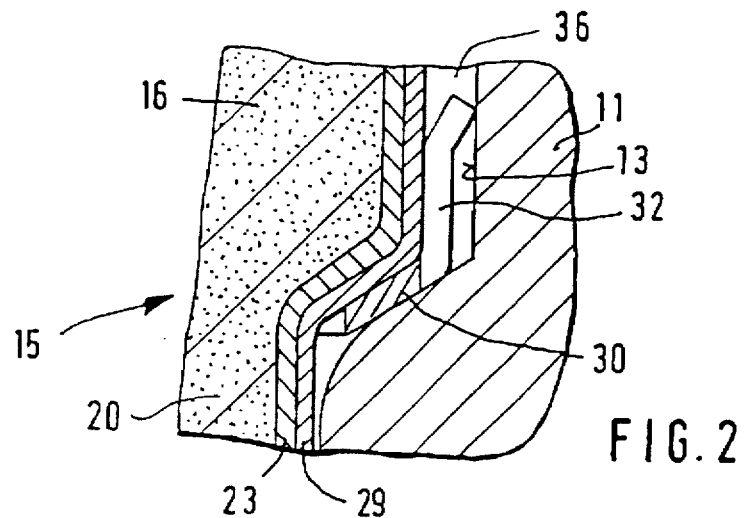
in FIG. 2, an enlarged section of the sealing zone X in FIG. 1.

The measuring sensor represented in FIG. 1 is a potential-free measuring sensor. Since the metallic seal ring is electrically conducting, the measuring electrode strip conductor 23 is covered, at least in the area of the sealing zone X, with an electrically insulating layer 29 (FIG. 2).

In place of an insulating layer 29 it is also possible to provide an electrically insulating layer system consisting of several layers. In the instant exemplary embodiment the insulating layer 29 is drawn around the circumference of the solid electrolyte body 20 which adjoins the housing 11. However, it is also conceivable to limit the insulating layer 29 merely to the area of the contact places of the seal ring 30, or to extend the insulating layer 29 on the side toward the gas to be measured as far as the protective layer 28. The insulating layer 29 is a plasma-sprayed magnesium-spinel layer.

Figure 4:
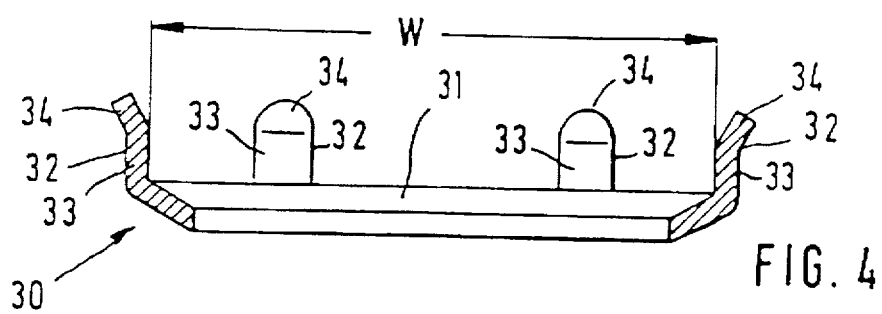
Figure 3:
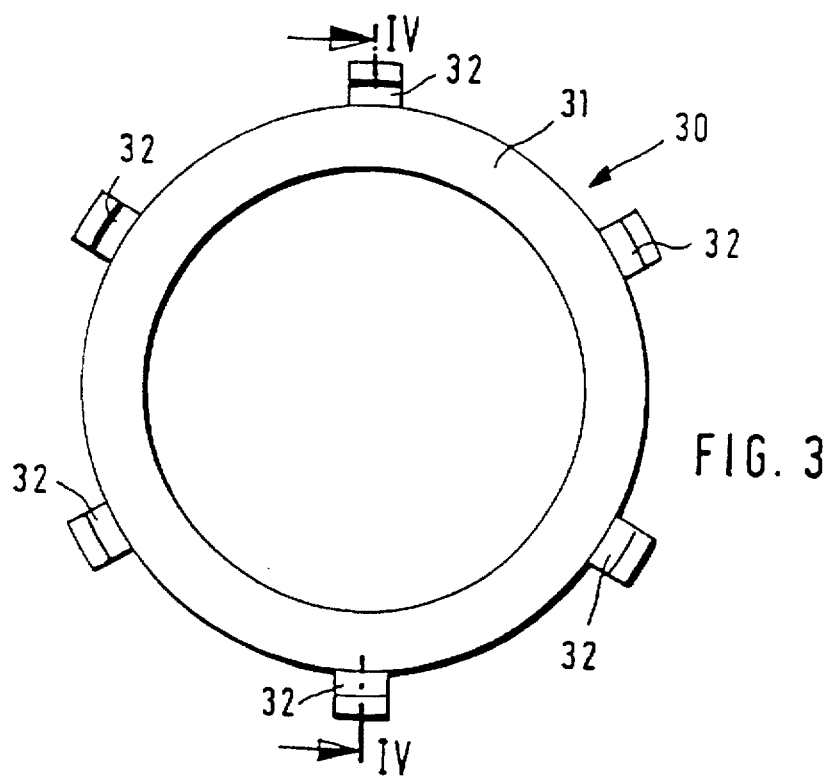
in FIG. 3, a top view of a seal ring and, in FIG. 4, a sectional representation along the line IV—IV in FIG. 3.

For fixation in place secure against relative rotation, the sensor element 15 is maintained under mechanical prestress in the housing 11 by means of the seal ring 30. For this purpose the seal ring 30 in FIGS. 3 and 4 has a ring element 31, on whose circumference strips 32 of a clear width W, which are resilient in the axial direction, are formed and project into the gap between the bead-shaped head 16 and the housing 11 (FIG. 2). In accordance with the instant exemplary embodiment, six resilient strips 32 are provided which are evenly disposed radially. The resilient strips 32 respectively have a lower part 33 and an outwardly angled part 34. The clear width W of the lower parts 33 is selected such that the lower parts 33 are seated under prestress on the bead-shaped head 16. Otherwise the gap 36 is of such size, or the upper parts 34 are outwardly angled sufficiently far, that the resilient strips 32 are supported on the interior wall of the longitudinal bore 13. By means of this it is assured that the sensor element 15 is held under mechanical prestress in the longitudinal bore 13 of the housing 11 by means of the seal rings 30 (FIG. 2). The exerted prestressing force maintains the sensor element 15 in the housing 11 so that, up to defined twisting force, it is fixed in place, secure against relative rotation, in the housing 11. This fixation in place, secure against relative rotation, is used to keep the sensor element in the radial orientation provided during assembly.

In the instant exemplary embodiment the seal ring 30 is made of Cr—Ni steel with a ductile layer of Ni or Cu applied to both sides. But it is also conceivable to employ other materials which permit the production of correspondingly resiliently embodied strips 32 and in addition assure sufficient sealing. However, the seal ring 30 is not limited to employment in connection with potential-free measuring sensors.

What is claimed is:

1. An electrochemical measuring sensor for determining the oxygen content of gases including exhaust gases of internal combustion engines, the electrochemical measuring sensor comprising:

a housing having an annular sealing seat defined on an inner surface thereof;

a sensor element which is comprised of a solid electrolyte body which is oxygen-ion conducting, which has a form of a tube having a closed end and which has an annular shoulder provided thereon; and a seal ring positioned between the annular sealing seat of the housing and the annular shoulder of the solid electrolyte body, and including a plurality of resilient elements distributed thereon, each of the plurality of resilient elements having a lower portion and an upper portion angled toward the housing, and the seal ring having a clear width so that each lower portion rests on and is mechanically prestressed against the annular shoulder of the sensor element and each upper portion is mechanically prestressed against the housing, whereby a tight seal of the sensor element to the housing is provided and the sensor element is maintained within the housing under mechanical prestress and secure against relative rotation.

2. The electrochemical measuring sensor in accordance with claim 1, wherein the seal ring consists of Cr—Ni steel having a ductile layer of Ni or Cu applied thereto.

3. The electrochemical measuring sensor in accordance with claim 1, wherein the seal ring further comprises a ring element onto which the plurality of resilient elements are evenly radially distributed thereon.

4. An electrochemical measuring sensor for determining the oxygen content of gases including exhaust gases of internal combustion engines, the electrochemical measuring sensor comprising:

a housing having an annular sealing seat defined on an inner surface thereof;

a sensor element which is comprised of a solid electrolyte body which is oxygen-ion conducting, which has a form of a tube having a closed end which contacts the gas to be measured and an open end which is inserted into the housing, and which has an annular shoulder provided near the open end; and a seal ring positioned between the annular sealing seat of the housing and the annular shoulder of the solid electrolyte body, the seal ring including a ring element and a plurality of resilient elements provided on the ring element and evenly radially distributed thereon, each of the plurality of resilient elements having a lower portion and an upper portion angled toward the housing, and the seal ring having a clear width so that each lower portion rests on and is mechanically prestressed against the annular shoulder of the sensor element and each upper portion is mechanically prestressed against the housing, whereby a tight seal of the sensor element to the housing is provided and the sensor element is maintained within the housing under mechanical prestress and secure against relative rotation.

5. The electrochemical measuring sensor in accordance with claim 4, wherein the seal ring consists of Cr—Ni steel having a ductile layer of Ni or Cu applied thereto.

* * * * *